United States Patent
Rahim (10) Patent No.: US 11,092,583 B2
(45) Date of Patent: Aug. 17, 2021

(54) MACHINE LEARNING STABILIZATION OF GAS SENSOR OUTPUT

(71) Applicant: AROMATIX, INC., Santa Clara, CA (US)

(72) Inventor: Chowdhury F. Rahim, Santa Clara, CA (US)

(73) Assignee: AROMATIX, INC., Santa Clara, CA (US)

( * ) Notice: Subject to any disclaimer, the term of this patent is extended or adjusted under 35 U.S.C. 154(b) by 168 days.

(21) Appl. No.: 16/445,515

(22) Filed: Jun. 19, 2019

(65) Prior Publication Data

US 2020/0400637 A1 Dec. 24, 2020

(51) Int. Cl.
*G01N 33/00* (2006.01)
*G06N 20/00* (2019.01)

(52) U.S. Cl.
CPC ......... *G01N 33/0075* (2013.01); *G06N 20/00* (2019.01)

(58) Field of Classification Search
None
See application file for complete search history.

(56) References Cited

U.S. PATENT DOCUMENTS

2005/0193832 A1* 9/2005 Tombs ................. G01F 1/8436
73/861

OTHER PUBLICATIONS

Xiang, ("Mobile Sensor Network Design and Optimization for Air Quality Monitoring," University of Michigan, 2014) (Year: 2014).*
Martin et al. ("Gas Sensing With Acoustic Devices", IEEE Ultrasonic Symposium, 1996, p. 423-434).*

* cited by examiner

*Primary Examiner* — Roy Y Yi
(74) *Attorney, Agent, or Firm* — Tyler Jeffs; Fabian VanCott (57) ABSTRACT

A system for stabilizing sensor readings. The system includes a processor; a memory communicatively coupled to the processor; a receiver to receive from a sensing device, a measurement and an environmental parameter. The system also includes a machine learning engine executed on the processor wherein the machine learning engine receives, as inputs: the environmental parameters; the measurement; and control parameters calculated based on control measurements made at time points before and after the measurement.

20 Claims, 5 Drawing Sheets

MACHINE LEARNING STABILIZATION OF GAS SENSOR OUTPUT

BACKGROUND

Gas sensors may be used to measure the concentration of a variety of gases. Humidity, the amount of water in the atmosphere, is an example of a gas sensor measurement. Atmospheric carbon dioxide is useful in a variety of environments, including smoke detectors, greenhouses, etc. Radon and carbon monoxide detectors are similarly useful to detect potential hazards in buildings.

BRIEF DESCRIPTION OF THE DRAWINGS

The accompanying drawings illustrate various examples of the principles described herein and are a part of the specification. The illustrated examples do not limit the scope of the claims.

Throughout the drawings, identical reference numbers designate similar, but not necessarily identical, elements. The figures are not necessarily to scale, and the size of some parts may be exaggerated or minimized to more clearly illustrate the example shown. The drawings provide examples and/or implementations consistent with the description. However, the description is not limited to the examples and/or implementations shown in the drawings.

DETAILED DESCRIPTION

Ultrasonic mass-based gas sensors are vulnerable to a variety of noise. Failing to address the noise may produce results which are not sufficiently accurate for the purpose of the sensor. Some types of noise, such as environmental noise may be compensated for by using secondary sensors, such as temperature and/or humidity sensors, coupled with machine learning. U.S. patent application Ser. No. 15/750,448, also available as PCT/US18/15734, describes examples of this approach to minimizing the noise from ultrasonic, mass-based gas sensor outputs.

However, not all noise sources are readily addressed with a secondary sensor to measure the noise source. The current specification describes systems and approaches for dealing with such noise, which is called herein, drift.

In general, drift has two manifestations. The first is spikes which occur over a short time frame and rapidly return to baseline. The second is random motion of the baseline, in either direction and with varying step sizes.

Mass-based ultrasonic gas sensors operate by vibrating an oscillator and counting the number of oscillations compared with a control value measured from a control oscillator. Adsorption of gas onto the oscillator alters the frequency. As more mass is absorbed, the oscillator slows down. When mass is released, the oscillator speeds up. This system is very sensitive and capable of detecting the low masses of atoms/molecules being adsorbed to the surface of the oscillator. In many examples, the control and the measurement oscillators have different surface chemistries to provide for preferential adsorption of a gas onto the surface of one oscillator relative to the other. The small size and low energy requirements of the oscillators favor using multiple oscillators and/or an array of oscillators to gather data.

Further, as the oscillators vibrate at megahertz frequencies, it is possible to get measurements at kilohertz or lower frequencies while still using independent counts for sequential measurements. However, most gas signals do not change rapidly on the kilohertz and/or megahertz time span. Accordingly, it is possible to use the knowledge of the gas profile and changes in gas concentrations to filter both spikes and drift from the results. Specific examples will be discussed below, but changes in gas concentration measurements with respect to time may be filtered to address both very fast changes and very slow changes based on the expected use of the sensor. This creates an intermediate band of changes which are accepted as actual changes in gas concentration. This approach has the advantage of limiting the need for processing power and model complexity, facilitating the use of small sensors and sensor processing systems, for example, those used with portable devices.

For example, with gas detection for the use of mold detection, there is a diffusion property of the measured gas(s) which limits the rate of change depending on the speed of the sensor. Accordingly, this secondary information may be used to correct for noise detected by the sensor but not indicative of changes in gas concentration, either because the rate of change is too fast or too slow.

As used in this specification and the associated claims, the computer readable storage medium may be a tangible device that retains and stores instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Among other examples, this specification describes a portable system for stabilizing sensor readings. The system includes a processor, a memory communicatively coupled to the processor, a receiver to receive from a sensing device, a measurement and an environmental parameter, and a machine learning engine executed on the processor. The machine learning engine receives, as inputs: the environmental parameters, the measurement, and control parameters calculated based on control measurements made at time points before and after the measurement.

Also described is a system for measuring gas with a gas sensor. The system includes a gas sensor which has a first mass-sensitive oscillator, a second mass-sensitive oscillator having a different surface chemistry from the first mass-sensitive oscillator, registers for accumulating counts of the first and second oscillators, an environmental sensor, and a transmitter. The system also includes a controller which includes a processor, a memory communicatively coupled to the processor which stores a set of measurements by the gas sensor and associated measurements by the environmental sensor, a receiver to receive information from the transmitter, a model generating engine to model the drift as a regular expression, and a machine learning (ML) engine to receive the measurement values of the regular expression, and output of the environmental sensor and t0 produce an output value.

This specification also describes a method of compensating for drift in a sensor. The method includes identifying a time series of measurements from the sensor, identifying a number of environmental measurements associated with each measurement of the time series of measurements from the sensor, assessing a residual error at a first time; assessing a residual error at a second time, modeling the residual error as a polynomial expression based on the residual error at the first time and the residual error at the second time, and providing values of the polynomial expression, the time series of measurements, and the number of environmental measurements associated with each measurement of the time series of measurements from the sensor to a machine learning (ML) system to reduce the impact of drift as defined by the residual error on the output of the machine learning system.

The present specification also describes a method of compensating for drift in a sensor output of a sensor. The method includes identifying a series of sensor outputs from the sensor; identifying multiple sensor outputs where a true value of the sensor is available; for each sensor output where a true value is available, calculate a residual offset for the sensor at that point; for each pair of sequential sensor outputs where a true value is available, create a linear model of the residual offset; and for each sensor output, identify the linear model of residual offset from the pair of sequential sensor outputs where a true value is available which bracket the sensor output and subtract a value from the linear model from the value of the sensor output to produce a drift compensated sensor output value.

Figure 1:
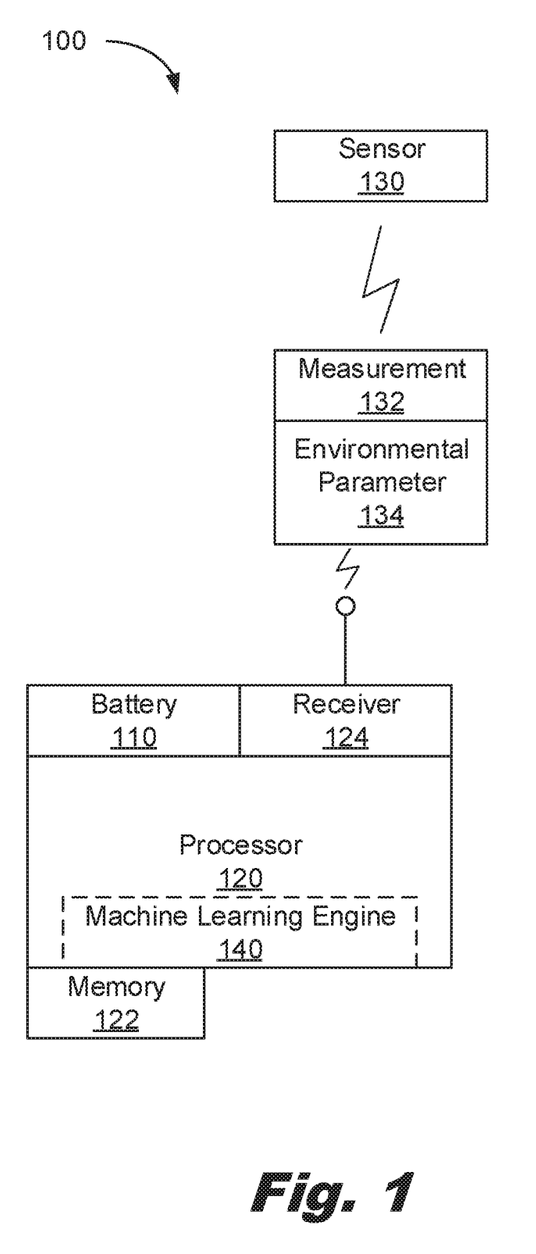
FIG. 1 shows a system for stabilizing sensor readings, consistent with this specification.

Turning now to the figures, FIG. 1 shows a system (100), which may be portable, for stabilizing sensor readings consistent with this specification. In general, the system (100) includes: a processor (120); a memory (122) communicatively coupled to the processor (120); a receiver (124) to receive from a sensor (130), a measurement (132) and an environmental parameter (134); a machine learning engine (140) executed on the processor (120) wherein the machine learning engine receives, as inputs: the environmental parameters (134); the measurement (132); and control parameters calculated based on control measurements made at time points before and after the measurement (132).

The system (100) may operate in a portable unit with minimal communication bandwidth. In some examples, the system (100) may operate without a lookup table.

The system (100) may include a battery to provide power for the system (100). In some examples, the system (100) lacks a direct power connection during use. In other examples, the system (100) may be plugged into an external power supply. The battery may be charged between uses. The battery may be charged during use. As used in this specification and the associated claims, the term battery indicates a power supply capable of function without being attached to a power grid. Examples of a battery include, a chemical battery as well as a solar cell, a generator, a fuel cell, and/or other non-grid based power source.

The processor (120) may be a single processor. The processor (120) may be a group of processors (120) which work together. The processor (120) may be part of a general purpose computer. The processor (120) may be a specific machine, for example, an Application Specific Integrated Circuit (ASIC).

The memory (122) may be a local memory, for example, a hard drive, flash drive, and/or similar. The memory (122) may also be a cloud based memory.

The system also includes a receiver (124) to receive information from the sensor (130). The receiver (124) may provide the information to the memory (122) to be stored. The information may be subsequently processed. The information may be processed in real time. In some examples, the information may be accumulated and then processed after a set amount of information is received. In an example, the system (100) may delay processing until a registration process is completed and/or some other control operations are performed.

The sensor (130) provides the signal to be processed. In some examples, the sensor (130) may be a mass-based oscillator to detect gas concentrations. While specific reference is made to a particular type of sensor, the sensor (130) may be another type of sensor (130) that is subject to drift.

The measurement (132) is the output of the sensor (130). The measurement (132) may be subject to preprocessing. The measurement (132) may be subject to smoothing in a number of ways. For example, the measurement (132) may be subject to smoothing in a physical dimension. Smoothing in a time and/or physical dimension may be performed before processing the measurements. Smoothing in a time and/or physical dimension may be performed after processing the measurements.

The environmental parameters (134) are measurements made with secondary sensors, that is, sensors besides the sensor (130). The environmental parameters include factors which may impact the output of the sensor (130). Examples of environmental parameters (134) include but are not limited to: temperature, humidity, pressure, secondary gas measurements, distance, vibration, speed, etc. Accordingly, a secondary sensor may be any sensor which measures these environmental parameters (134).

The control parameters are parameters which model the actual value. For example control parameters may be a linear model of the gas concentration. Control parameters may be expressed as a series of values, for example, as a polynomial series. The control parameters may include exponential, periodic, and/or other non-polynomial factors. In practice, the use of a polynomial series of a first and/or second order may be sufficient to provide the desired accuracy without excessive overhead which may increase processing demands, memory demands, power consumption, and/or other resources.

In an example, the control parameters are a linear interpolation between a time point before and a time point after the measurement (132). The control parameters may be a polynomial. For example, the polynomial may be a second order polynomial.

The control parameters are determined based on measurements (132) at time points. The time points may be before, between, and/or after the measurements (132) of interest. For example, the sensor (130) may measure a control region before and after conducting a measurement of an area of interest. The true value in control region may be static. This allows the drift to be calculated from the measurements before the area of interest and after measurement (132) of the area of interest.

The time points may include time points before the measurement (132). The time points may include time points after the measurement (132). The time points may include time points interspersed with the measurement (132). In an example, time points before and after the measurements are used to form linear control parameters, i.e., a slope and/or an offset. In an example, time points before, after, and interspersed with the measurements (132) are used to calculate control parameters as a second order polynomial.

In some examples, the time points before and after are taken at a same physical location. For example, the before and after time points may be taken at a registration position. The registration position may have a constant expected signal level. For example, the registration position may have a constant gas composition for a gas sensor.

In some examples, the system (100) filters transients with an absolute value of d[concentration]/dt that is greater than a threshold. A transient is a short term, unexplained excursion of the measured value from baseline. For example, filtered transients may be those which have a change in concentration per unit time greater than a threshold which represents the maximum rate of change for a physical system being assessed. For example, the motion of the sensor may limit the rate of change in gas concentration due to the presence of a diffusion profile around sources/sinks of the gas. Further, the short-term, high speed transients may return to as similar baseline after a relatively short period of time. Accordingly, they may be filtered out.

Figure 2:
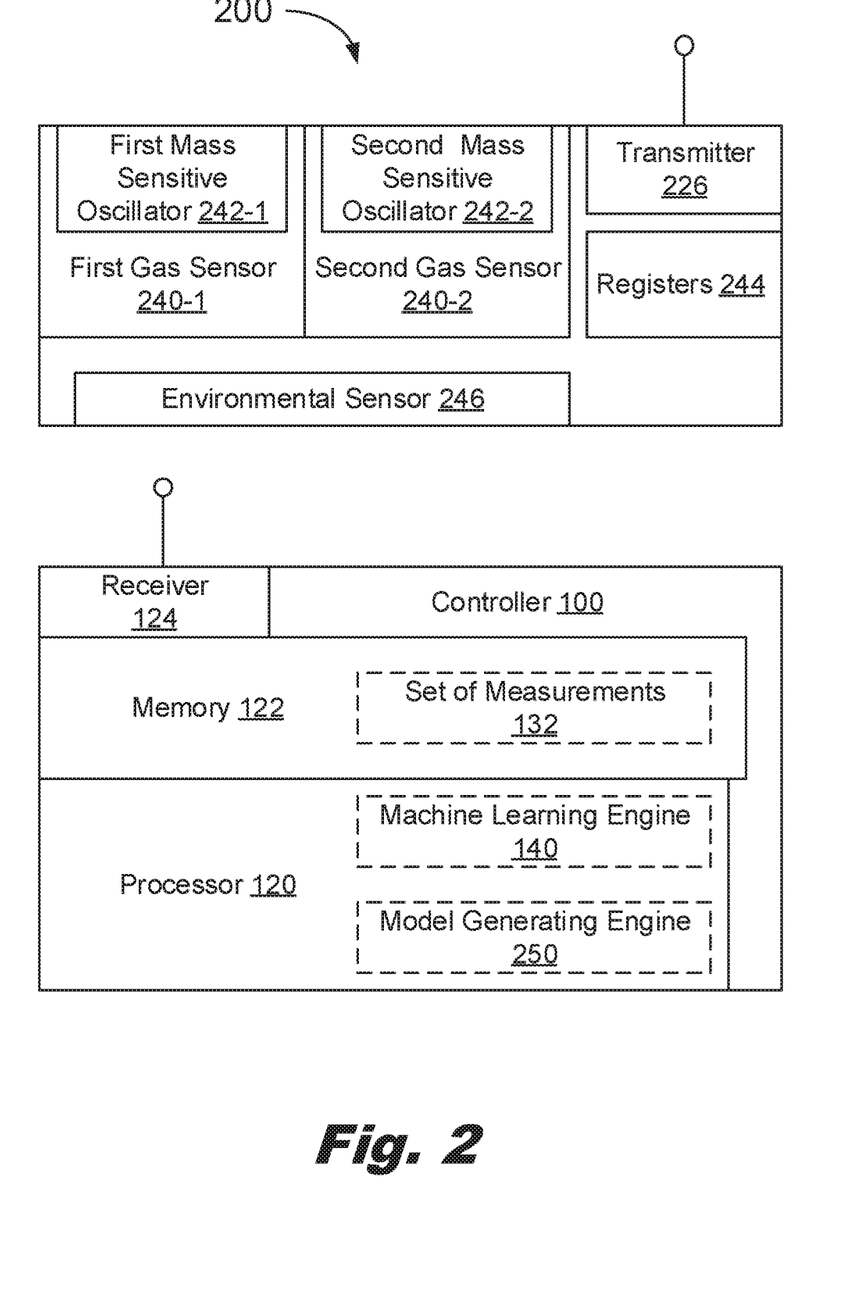
FIG. 2 shows a system for measuring gas with a vibration sensor, consistent with this specification.

FIG. 2 shows a system (200) for measuring gas consistent with this specification. The system (200) includes: a first gas sensor (240-1) including: a first mass-sensitive oscillator (242-1); a second gas sensor (240-2) including: a second mass-sensitive oscillator (242-2) having a different surface chemistry from the first mass-sensitive oscillator (242-1); registers (244) for accumulating counts of the first and second oscillators (242), an environmental sensor (246), and a transmitter (226); a controller (100) including: a processor (120), a memory (122) communicatively coupled to the processor (120) comprising a set of measurements (132) by the gas sensor (240) and associated measurements (134) by the environmental sensor (246); a receiver (124) to receive information from the transmitter (226); a model generating engine (250) to model the drift as a regular expression; and a machine learning (ML) engine (140) to receive the set of measurements (132), values of the regular expression, and output of the environmental sensor (246) and produce an output value.

The system (200) includes both sensors (240) and a controller (100). The sensor includes a transmitter (226) to transmit information from the oscillator(s) (242) to a receiver (124) associated with the controller (100). The controller (100) includes a processor (120), a memory (122), a model generating engine (250) and a machine learning engine (140). The two engines (140, 250) use the processor (120) to perform their operations.

The transmitter (226) transmits the output of the gas sensors (240) to the receiver (124). The receiver (124) then provides the results to the model generating engine (250) and machine learning engine (140) to form the model for the drift and calculate the output value respectively. The transmitter (226) and receiver (124) may use any particular method of communications which is suitable for the system (200). In some examples, a short range wireless protocol is preferable. In an example, the Bluetooth(tm) protocol is used. In another example, the IEEE 802.11 WIFI protocol is used. Other protocols, such as IEEE 8016 and/or IEEE 802.15.4 may be used.

The gas sensors (240) include oscillators (242) with differing surface chemistries. The different surface chemistries allow for differential behavior with respect to molecules which interact with one of the surface chemistries. In an example, the surface chemistries have differential interaction with $CO_2$, water, and/or some other molecule to be detected. While FIG. 2 depicts two gas sensors (240), the system (200) may include more than two gas sensors (240).

In an example, a gas sensor (240) includes an array of oscillators (242). The array of oscillators (242) may include replicates. The array of oscillators (242) may include multiple species-specific surface chemistries. The array of oscillators (242) may operate at multiple frequencies to provide additional differentiation. For example, two oscillators (242) may operate at a first frequency and two oscillators (242) may operate at a second frequency. The first and second frequencies may be related to each other. In an example, the second frequency is a harmonic of the first frequency.

Each register (244) may accumulate a count of oscillations for an oscillator (242). In an example, a register accumulates a difference between two oscillators (242) with a first oscillator (242) incrementing the register (244) and a second oscillator (242) decrementing the register (244).

The environmental sensor (246) measures an environmental property and reports that environmental property. The environmental sensor (246) may measure temperature, humidity, light, proximity, etc. The environmental property measurements are used as inputs into the machine learning (ML) engine (140) to calculate the actual output of the gas sensor (240).

The receiver (124) is associated with a processor (120) and a memory (122). The processor (120) also supports two engines (140, 250). The processor (120) supports the model generating engine (250) to model the drift as a regular expression. The processor (120) supports the machine learning (ML) engine (140) to receive the measurement (132), values of the regular expression, and output of the environmental sensor (244) and produce an output value.

The model generating engine (250) models the drift. The model may be a polynomial model. The model may include exponential terms, derivative terms, periodic terms, etc. It has been found that a first and/or second order polynomial model may provide adequate modeling of drift over the relevant time frames. This offers the advantage of a compact model characterized by a small number of factors, for example, a slope and/or a slope and an offset. The use of a first and second order models allows reduced complexity for the machine learning portion of the calculation performed by the machine learning engine (140). For example, use of a linear model may be compensated for prior to providing the values into the machine learning engine (140). This may decouple the issue of drift from the other calculations limiting the processing power demands, memory resources consumed, and/or other resource consumption.

The model generating engine (250) may format the model in regular expression. In an example, the regular expression is a polynomial expansion. The polynomial expansion may be a first order expansion. The polynomial expansion may be a second-order expansion. The polynomial expansion may be a third order or higher order expansion. The model generating engine (250) may use a least squares fit and/or similar technique to estimate the drift at various time points of the model. In an example, the model generating engine (250) identifies a first time point with a first known gas concentration and a second time point with a second known gas concentration and generates a linear model between the first and second time points. In some examples, the first and second known gas concentrations are the same gas concentration, for example, the gas concentration at a reference and/or control location.

This approach may also bypass the need for a lookup table and/or similar data storage requirement. Instead, the modeled drift is compensated for directly without reference to additional machine learning models with their overhead and communication requirements.

The machine learning engine (140) takes the measurement, the model variables, and environmental variables and calculates the gas concentration. In some examples, as discussed above, the model variables are used to modify the measurement value(s) prior to processing by the machine learning engine (140). In other examples, the machine learning engine also receives and processes the model variables.

In some examples, the inputs to the machine learning model are limited to the measurement, values of the regular expression, and outputs from a number of environmental sensors.

The system (200) may not include a look-up table. For example, the system may have limited or no communication to external networks. As a particular example, the system (200) may be a stand-alone system. The controller (100) may be a portable device which operates on a power supply, e.g., a battery. The controller (100) may be able to removably power itself to a network, for example to recharge. The controller (100) may be static during use and/or may move during use. In an example, the controller (100) comprises a cellular phone, a laptop, a tablet, and/or similar processor with an associated module. The module may contain an ASIC. The module may contain a memory. The controller (100) may include a user interface to allow control over the sensor (130).

In some examples, the system (100) is partially defined by the components excluded. Excluding these components may reduce costs. Excluding these components may reduce network demands. In an example, the system (100) does not include a look-up table. The system (100) may not have a network connection. The system (100) may not have a power connection to a power supply besides the onboard battery.

Figure 3:
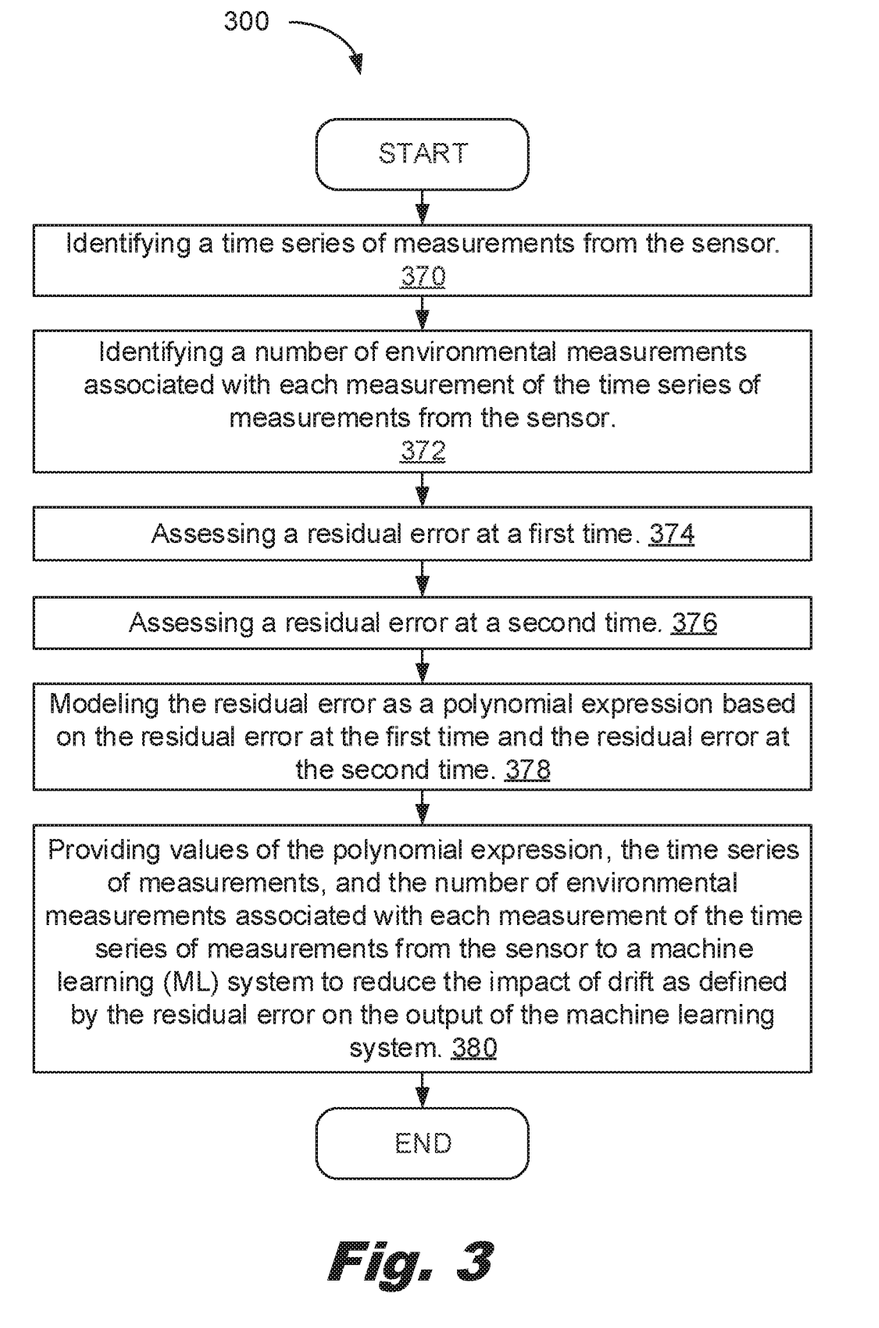
FIG. 3 shows a flowchart for a method of compensating for drift in a sensor, consistent with this specification.

FIG. 3 shows a flowchart for a method (300) of compensating for drift in a sensor consistent with this specification. The method (300) includes: identifying (370) a time series of measurements from the sensor; identifying (372) a number of environmental measurements associated with each measurement of the time series of measurements from the sensor; assessing (374) a residual error at a first time; assessing (376) a residual error at a second time; modeling (378) the residual error as a polynomial expression based on the residual error at the first time and the residual error at the second time; and providing (380) values of the polynomial expression, the time series of measurements, and the number of environmental measurements associated with each measurement of the time series of measurements from the sensor to a machine learning (ML) system to reduce the impact of drift as defined by the residual error on the output of the machine learning system.

The method (300) includes identifying (370) a time series of measurements from the sensor. The time series of measurements includes measurements where the residual error is either zero and/or constant. For example, the true value of the gas concentration may be known. In another example, the gas concentration at a location, such as a control location, may be constant at multiple time points, without being zero. The sensor (130) may be placed at the control location before and after measurements of other locations. The sensor (130) may be placed at the control location periodically through the time series of measurements. These periods may then be used to control for the drift using the method (300).

The method (300) includes identifying (372) a number of environmental measurements associated with each measurement of the time series of measurements from the sensor. The method includes using at least one environmental sensor, for example, a temperature, pressure, humidity, distance, proximity, and/or other sensor to measure environmental measurements. These environmental measurements are provided to the machine learning engine (140) to produce an output.

The method (300) includes assessing (374) a residual error at a first time. The residual error may be baselined (tared) to zero. The residual error may be determined and subtracted from future measurements.

The method (300) includes assessing (376) a residual error at a second time. The first and second times may bracket the times when the other measurements are being made. For example, the first time may be before measurements in the time series are made. The second time may be after measurements in the time series are made. The first and/or second time may be during the time series of measurements. Preferably, the first and second times are close to the time when the time series of measurements is made to reduce the impact of drift on the final values.

The method (300) includes modeling (378) the residual error as a polynomial expression based on the residual error at the first time and the residual error at the second time. The polynomial expression may be a regular expression. The polynomial expression may be first order, second order, third order, etc. The polynomial expression may be expressed as $Drift \sim = A + B(t) + C(t^2) + D(t^3)$, where A, B, C, and D are constants and t is a time index for a time series of measurements. A, B, C, and D are then provided as inputs to the machine learning engine (140). Different orders of polynomial expression may have different numbers of constants to provide to the machine learning engine (140).

The method (300) includes providing (380) values of the polynomial expression, the time series of measurements, and the number of environmental measurements associated with each measurement of the time series of measurements from the sensor to a machine learning (ML) (140) system to reduce the impact of drift as defined by the residual error on the output of the machine learning system.

The method (300) may also include additional actions. The method (300) may be performed without certain additional actions. For example, the method (300) may be performed without retrieval of data from a look-up table.

In an example, modeling the residual error as a polynomial expression based on residual error at the first time and residual error at the second time comprises a linear regression of the residual error at the first time and the residual error at the second time.

The method (300) may include identifying a number of measurements taken at time points between the first time and the second time wherein the modeling the residual error as a polynomial expression based on residual error at the first time and residual error at the second time comprises a least squares fit between calculate residual error for the number of measurements taken at time points between the first time and the second time. In an example, the number of measurements number of measurements taken at time points between the first time and the second time have a shared value and residual errors may be determined from the shared value and the measurements. The shared value may be zero. The shared value may be non-zero.

Figure 4:
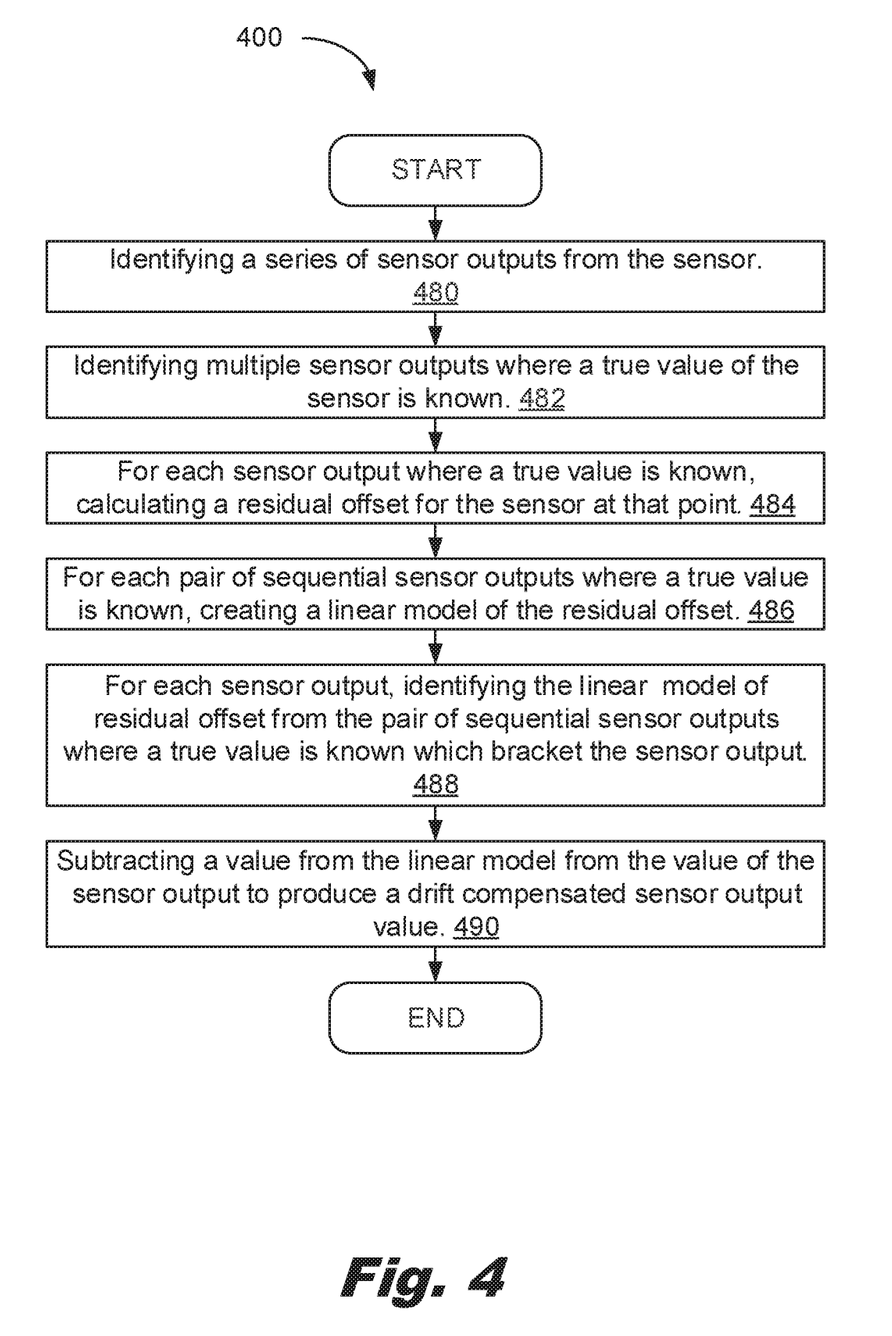
FIG. 4 shows a flowchart for a method of compensating for drift in a sensor, consistent with this specification.

FIG. 4 shows a flowchart for a method (400) of compensating for drift in a sensor output of a sensor consistent with this specification. The method (400) includes: identifying (480) a series of sensor outputs (132) from the sensor (130); identifying (482) multiple sensor outputs where a true value of the sensor is known, for each sensor output where a true value is known, calculating (484) a residual offset for the sensor at that point; for each pair of sequential sensor outputs where a true value is known, creating (486) a linear model of the residual offset; for each sensor output, identifying (488) the linear model of residual offset from the pair of sequential sensor outputs where a true value is known which bracket the sensor output; and subtracting (490) a value from the linear model from the value of the sensor output to produce a drift compensated sensor output value.

The method (400) includes identifying (480) a series of sensor outputs, i.e., measurements (132) from the sensor (130). The series of sensor measurements (132) may be a time series of measurements. The series of sensor measurements (132) may be a positional series. The series of sensor measurements (132) may be equally spaced. The series of sensor measurements (132) may be unequally spaced in space and/or time.

The method (400) includes identifying (482) multiple sensor outputs (132) where a true value of the sensor (130) is known. These control values may be provided by controlling inputs to the sensor. For example, a known gas concentration may be passed over the sensor (130). A known ambient gas concentration may be measured.

The method (400) includes, for each sensor output (132) where a true value is known, calculating (484) a residual offset for the sensor (130) at that point. The residual is the difference between the known value and the calculated value. The residual offset may also be known as a residual error.

The method (400) includes, for each pair of sequential sensor outputs where a true value is known, creating (486) a linear model of the residual offset. Using sequential pairs allows the use of information closely related to the measurements in time and/or space. This may reduce the impact of time on drift, reducing the amount of drift which needs to be accounted for.

The method (400) includes, for each sensor output (132), identifying (488) the linear model of residual offset from the pair of sequential sensor outputs where a true value is known which bracket the sensor output. The linear model of residual offset may be a first order polynomial model of the residual offset.

The method (400) includes subtracting (490) a value from the linear model from the value of the sensor output to produce a drift compensated sensor output value. This may be performed prior to providing the values to a machine learning engine (140) and/or after providing the values to the machine learning engine (140). Preprocessing by subtracting the calculated residual error at each point has the advantage of reducing the complexity of the system being modeled by the machine learning engine (140), which, in turn, increases the effectiveness of the machine learning engine (140).

Figure 5A:
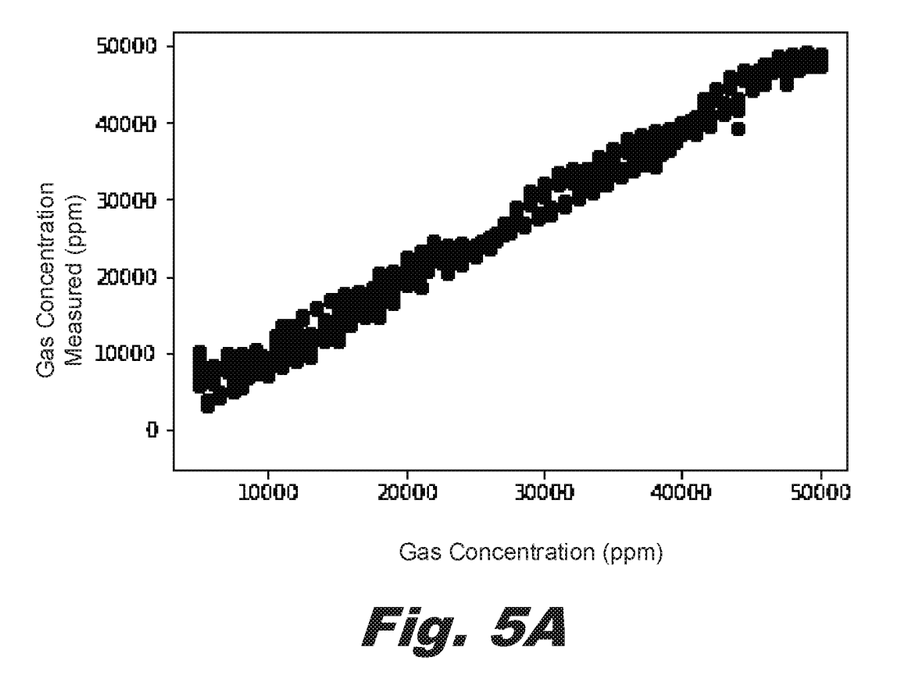
FIG. 5A shows raw sensor data during an increasing gas concentration and FIG. 5B shows the same sensor data after being processed in a method consistent with this specification.
Figure 5B:
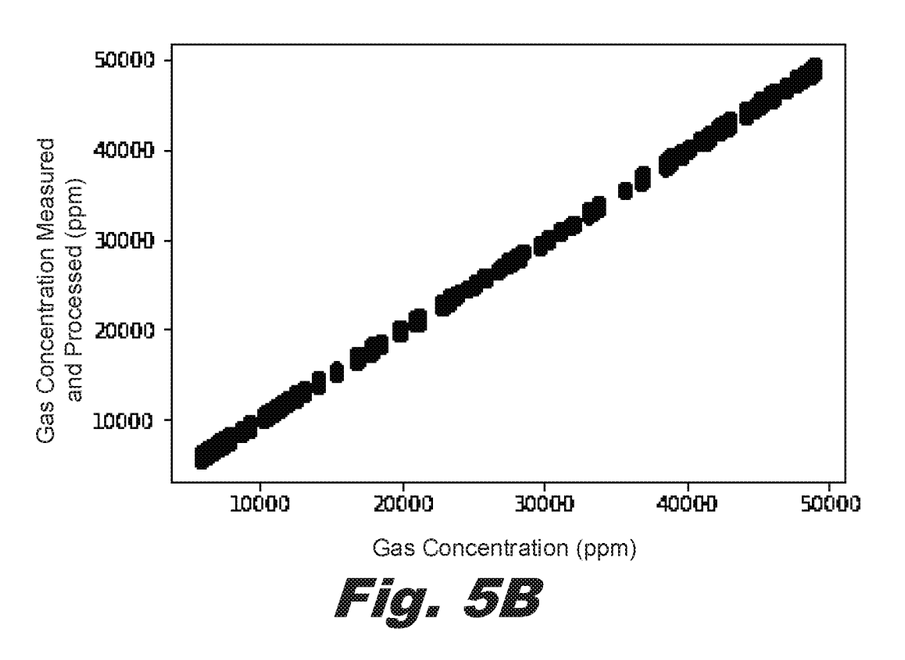

FIG. 5A shows raw sensor data during an increasing gas concentration and FIG. 5B shows the same sensor data after being processed in a method consistent with this specification. The horizontal axis is the actual value of the test gas in parts per million (ppm). The vertical axis is the measurements from an ultrasound based gas sensor. FIG. 5A is the uncorrected data and FIG. 5B is after processing with the approach described in the present specification. As can be seen, the variation in the values is greater in FIG. 5A compared with FIG. 5B. FIG. 5B also shows greater linearity compared with the actual values.

It will be appreciated that, within the principles described by this specification, a vast number of variations exist. It should also be appreciated that the examples described are only examples, and are not intended to limit the scope, applicability, or construction of the claims in any way.

What is claimed is:

1. A system for stabilizing sensor readings, the system comprising:
   a processor;
   a memory communicatively coupled to the processor;
   a receiver to receive from a sensing device, a measurement and an environmental parameter;
   a machine learning engine executed on the processor wherein the machine learning engine receives, as inputs:
      the environmental parameters;
      the measurement at a location of interest; and
      control parameters calculated by:
         taking a control measurement at a control location before taking the measurement at the area of interest:
         taking a control measurement at the control location after taking the measurement at the area of interest; and
         interpolating between the control measurements.

2. The system of claim 1, wherein the control parameters are a linear interpolation between a time point before and a time point after the measurement.

3. The system of claim 1, wherein the control parameters are a polynomial model.

4. The system of claim 3, wherein the polynomial model is a second order polynomial model.

5. The system of claim 1, wherein the measurement is subjected to smoothing in a physical dimension.

6. The system of claim 1, wherein the system operates without a lookup table.

7. The system of claim 1, wherein the control measurements are taken at a same geometrical position and a same expected signal level.

8. The system of claim 1, wherein the system filters transients with an absolute value of d/dt is greater than a threshold.

9. A system for measuring gas, the system comprising:
   a gas sensor comprising:
      a first mass-sensitive oscillator;
      a second mass-sensitive oscillator having a different surface chemistry from the first mass-sensitive oscillator;
      registers for accumulating counts of the first and second oscillators;
      an environmental sensor; and
      a transmitter;
   a controller comprising:
      a processor;
      a memory communicatively coupled to the processor, the memory to store a set of measurements by the gas sensor and associated measurements by the environmental sensor;
      a receiver to receive information from the transmitter; and
      a machine learning (ML) engine to receive the measurement and output of the environmental sensor and produce an output value by:
         identifying gas sensor measurements for which a control value exists;
         for each gas sensor measurement where a control value exists, determining a residual offset for the gas sensor output between the measurement and the control value;
         for each pair of sequential measurements where a control value exists, creating a linear model of the residual offset;
         identifying, for each pair of sequential measurements where the control value exists, sensor outputs that are bracketed by the sequential measurements; and
         subtracting a value from the linear model from a bracketed sensor output.

10. The system of claim 9, wherein the regular expression is a polynomial expression.

11. The system of claim 10, wherein the polynomial expression is a third-order polynomial expression.

12. The system of claim 9, wherein inputs to the machine learning model include just the measurement, values of the regular expression, and outputs from a number of environmental sensors.

13. A method of compensating for drift in a sensor comprising:
   identifying a time series of measurements from the sensor;

identifying a number of environmental measurements associated with each measurement of the time series of measurements from the sensor;

assessing a residual error at a first time, wherein the first time is before the time series of measurements from the sensor;

assessing a residual error at a second time, wherein the second time is after the time series of measurements from the sensor;

modeling the residual error as a polynomial expression based on the residual error at the first time and the residual error at the second time; and providing values of the polynomial expression, the time series of measurements, and the number of environmental measurements associated with each measurement of the time series of measurements from the sensor to a machine learning (ML) system to reduce the impact of drift as defined by the residual error on the output of the machine learning system.

14. The method of claim 13, wherein the method does not comprise retrieval of data from a look-up table.

15. The method of claim 13, wherein modeling the residual error as a polynomial expression based on residual error at the first time and residual error at the second time comprises executing a linear regression between the residual error at the first time and the residual error at the second time.

16. The method of claim 13, further comprising identifying a number of measurements taken at time points between the first time and the second time wherein modeling the residual error as a polynomial expression based on residual error at the first time and residual error at the second time comprises performing a least squares fit between calculated residual errors for the number of measurements taken at time points between the first time and the second time.

17. The method of claim 16, wherein the number of measurements taken at time points between the first time and the second time have a shared value and residual errors are determined from the shared value and the measurements.

18. The method of claim 17, wherein the shared value is zero.

19. The method of claim 17, wherein the shared value is non-zero.

20. The system of claim 1, wherein the control parameters are further calculated by taking a control measurement at the control location interspersed between taking measurements at the area of interest.

* * * * *